United States Patent
Morimoto et al.

(10) Patent No.: US 8,580,281 B2
(45) Date of Patent: Nov. 12, 2013

(54) MEDICATED PATCH

(75) Inventors: Kumi Morimoto, Tsukuba (JP); Akio Takeuchi, Tsukuba (JP); Takashi Yasukochi, Tsukuba (JP); Kaori Yamaguchi, Tsukuba (JP); Kenji Ishigaki, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 213 days.

(21) Appl. No.: 12/919,723

(22) PCT Filed: Feb. 9, 2009

(86) PCT No.: PCT/JP2009/052175
§ 371 (c)(1),
(2), (4) Date: Sep. 13, 2010

(87) PCT Pub. No.: WO2009/107476
PCT Pub. Date: Sep. 3, 2009

(65) Prior Publication Data
US 2011/0008398 A1 Jan. 13, 2011

(30) Foreign Application Priority Data
Feb. 27, 2008 (JP) .................................. 2008-046804

(51) Int. Cl.
A61K 9/00 (2006.01)
A61F 13/02 (2006.01)
A61F 13/00 (2006.01)

(52) U.S. Cl.
USPC ............................. 424/400; 424/448; 424/449

(58) Field of Classification Search
USPC ........................................................ 424/400
See application file for complete search history.

(56) References Cited

U.S. PATENT DOCUMENTS

| | | | |
|---|---|---|---|
| 5,059,189 A | 10/1991 | Cilento et al. | |
| 5,676,968 A | 10/1997 | Lipp et al. | |
| 5,807,570 A | 9/1998 | Chen et al. | |
| 5,830,497 A | 11/1998 | Yamanaka et al. | |
| 6,207,183 B1 * | 3/2001 | Horstmann et al. | 424/448 |
| 6,620,429 B1 * | 9/2003 | Muller | 424/449 |
| 6,638,528 B1 | 10/2003 | Kanios | |
| 6,884,434 B1 | 4/2005 | Muller et al. | |
| 6,899,894 B1 | 5/2005 | Klein et al. | |
| 7,150,881 B2 * | 12/2006 | Govil et al. | 424/449 |
| 7,175,853 B1 | 2/2007 | Bracht | |
| 7,921,999 B1 | 4/2011 | Kimball | |
| 2002/0192243 A1 | 12/2002 | Hsu et al. | |
| 2003/0180347 A1 * | 9/2003 | Young et al. | 424/449 |
| 2004/0096491 A1 | 5/2004 | Tateishi et al. | |
| 2004/0220262 A1 | 11/2004 | Hsu et al. | |
| 2005/0074487 A1 | 4/2005 | Hsu et al. | |
| 2007/0098772 A1 * | 5/2007 | Westcott et al. | 424/449 |
| 2009/0220580 A1 | 9/2009 | Kawahara et al. | |
| 2010/0062046 A1 | 3/2010 | Allen et al. | |
| 2011/0086086 A1 | 4/2011 | Johnson et al. | |

FOREIGN PATENT DOCUMENTS

| | | |
|---|---|---|
| EP | 0387751 * | 9/1990 |
| EP | 0 887 075 A2 | 12/1998 |
| EP | 1 743 645 A1 | 1/2007 |
| JP | H7-506083 | 7/1995 |
| JP | H1135452 | 2/1999 |
| JP | H1147233 | 2/1999 |
| JP | 11-506462 A | 6/1999 |
| JP | 2001-518058 A | 10/2001 |
| JP | 2002-509874 A | 4/2002 |
| JP | 2002-509878 A | 4/2002 |
| JP | 2002-509879 A | 4/2002 |
| JP | 2004-83523 A | 3/2004 |
| JP | 2005-528413 A | 9/2005 |
| JP | 2005-535686 A | 11/2005 |
| JP | 2007-016020 A | 1/2007 |
| JP | 2007-16020 A | 1/2007 |
| JP | 2007031436 | 2/2007 |
| JP | 2007-176880 A | 7/2007 |
| WO | 93/08795 | 5/1993 |
| WO | 96/39136 A1 | 12/1996 |
| WO | 01/43734 A2 | 6/2001 |
| WO | 02/45701 A2 | 6/2002 |
| WO | 02/069942 A1 | 9/2002 |
| WO | 2006/040680 A1 | 4/2006 |
| WO | 2006/082728 A1 | 8/2006 |
| WO | 2006/114868 A1 | 11/2006 |
| WO | 2007/012963 A1 | 2/2007 |
| WO | 2007/094385 A1 | 8/2007 |
| WO | 2007/129712 A1 | 11/2007 |
| WO | 2008/032678 A1 | 3/2008 |

OTHER PUBLICATIONS

Extended European Search Report issued on Mar. 31, 2011, in counterpart European Patent Application No. 09715635.0.
Extended European Search Report issued on Mar. 31, 2011, in related European Patent Application No. 09715476.9.
Extended European Search Report issued on Apr. 6, 2011, in related European Patent Application No. 09715573.3.
International Preliminary Examination Report for corresponding PCT Application No. PCT/JP2009/052180; 9 pages; includes the PCT/IB/338, the PCT/IB/373, and the PCT/ISA/237; mailed on Oct. 14, 2010.
International Preliminary Examination Report for a related PCT Application No. PCT/JP2009/052181; 8 pages; includes the PCT/IB/338, the PCT/IB/373, and the PCT/ISA/237; mailed on Oct. 14, 2010.
International Preliminary Examination Report for a related PCT Application No. PCT/JP2009/052175; 6 pages; includes the PCT/IB/338, the PCT/IB/373, and the PCT/ISA/237; mailed on Oct. 14, 2010.
International Preliminary Examination Report for a related PCT Application No. PCT/JP2009/052177; 5 pages; includes the PCT/IB/338, the PCT/IB/373, and the PCT/ISA/237; mailed on Oct. 14, 2010.
Final Office Action for U.S. Appl. No. 12/919,739, issued on Sep. 12, 2012.
"The Japanese Pharmacopoeia", Mar. 31, 2006; p. 31.

* cited by examiner

*Primary Examiner* — Blessing Fubara
*Assistant Examiner* — Jennifer Berrios
(74) *Attorney, Agent, or Firm* — Nath, Goldberg & Meyer; Sheldon M. McGee

(57) ABSTRACT

Provided is a medicated patch containing a medicinal agent and an adhesive base material and having an acid value of no greater than 28, where the medicinal agent is varenicline or a pharmaceutically acceptable salt of varenicline.

10 Claims, 12 Drawing Sheets

MEDICATED PATCH

This is a National Phase Application filed under 35 U.S.C. 371 as a national stage of PCT/JP2009/052175, filed Feb. 9, 2009, an application claiming foreign priority benefits under 35 USC 119 of Japanese Application No. 2008-046804, filed on Feb. 27, 2008, the content of each of which is hereby incorporated by reference in its entirety.

TECHNICAL FIELD

The present invention relates to a medicated patch.

BACKGROUND ART

Various types of medicated patches containing medicinal agents are being developed with expectations of reducing side-effects caused by tissue absorption of the medicinal agents into the gastrointestinal tract and avoiding first pass into the liver, and of improving patient compliance.

However, not all medicinal agents exhibit satisfactory tissue absorption with transdermal administration, transmucosal administration or transnail administration, and much investigation has been conducted to improve tissue absorption.

Medicinal agents are available on the market in the form of acid addition salts, from the viewpoint of handleability and stability. However, it is generally known that when medicinal agents of acid addition salts are directly applied by transdermal administration, their tissue absorption tends to be lower. On the other hand, it is also known that free bases (free forms) of medicinal agents are preferred for tissue absorption.

Methods of neutralizing (desalting) acid addition salts of medicinal agents to be used in medicated patches, using metal hydroxides such as sodium hydroxide, as strong bases which completely desalt the acid addition salts, have been investigated (Patent documents 1 and 2, for example), but all of these methods either eliminate beforehand the metal salts produced by filtration treatment, or mix them with adhesive base materials.

[Patent document 1] Japanese Unexamined Patent Application Publication No. 2007-16020
[Patent document 2] Japanese Unexamined Patent Application Publication (Translation of PCT Application) No. 2002-509874

DISCLOSURE OF THE INVENTION

Problems to be Solved by the Invention

The present inventors have found, however, that when a medicinal agent free form and metal salt (sodium chloride or the like) are formed by neutralization reaction of the acid addition salt of the medicinal agent, and the metal salt is neutralized together with an adhesive base material without removal by filtration treatment, for application of a more convenient production method, the production stability and production properties of the medicated patch tend to be reduced.

Furthermore, the present inventors found that when varenicline or a pharmaceutically acceptable salt of varenicline is used as the medicinal agent, coloration-causing reactions also occur in addition to the problems mentioned above, and that it is often not possible to obtain sufficient stability and absorption properties as a medicated patch.

It is therefore an object of the present invention to provide a medicated patch comprising varenicline or a pharmaceutically acceptable salt of varenicline as the medicinal agent, having high cutaneous permeability for the medicinal agent, and having excellent pharmaceutical stability and pharmaceutical properties.

Means for Solving the Problems

As a result of much diligent research directed toward achieving the object stated above, the present inventors have found that, even when varenicline or a pharmaceutically acceptable salt of varenicline is contained as the medicinal agent, adjustment of the acid value of the medicated patch to a specified value can yield a medicated patch having high cutaneous permeability and excellent pharmaceutical stability.

Specifically, the invention provides a medicated patch comprising a medicinal agent and an adhesive base material and having an acid value of no greater than 28, wherein the medicinal agent is varenicline or a pharmaceutically acceptable salt of varenicline.

The acid value of the medicated patch is the value calculated by the following formula (1), according to the Japanese Pharmacopeia.

[Formula 1]

$$\text{Acid value} = [56.11 \text{ (g/mol)} \times \text{amount of potassium hydroxide necessary for neutralization (mol)}] / \text{medicated patch weight 100 (mg)} \quad (1)$$

Since the acid value of the medicated patch is limited as explained above according to the invention, decomposition of the medicinal agent in the medicated patch is presumably inhibited and the pharmaceutical stability is thereby improved. Also according to the invention having the construction described above, the tissue permeability (especially cutaneous permeability) of the medicinal agent is drastically improved.

The medicated patch of the invention has a pH of preferably 7.5 or higher and more preferably 9.0 or higher. The pH of the medicated patch is the pH of an aqueous solution obtained by mixing the medicated patch in water to dissolve the water-soluble components. If the pH of the medicated patch is 7.5 or higher, the cutaneous permeability will tend to be significantly improved.

According to the invention, the adhesive base material is preferably an acrylic-based polymer. The acrylic-based polymer is not particularly restricted so long as the acid value of the medicated patch is no greater than 28, but it preferably contains no carboxyl groups. Such an acrylic-based polymer will allow the acid value to be easily reduced below the prescribed value, so that the pharmaceutical stability can be even further improved. The acrylic-based polymer also preferably has a hydroxyl group. Such an acrylic-based polymer can further improve the tissue permeability (cutaneous permeability) of the medicinal agent. The acrylic-based polymer also preferably contains no vinyl acetate as a monomer unit. Such an acrylic-based polymer can further inhibit decomposition of the medicinal agent in the medicated patch, and prevent coloration of the medicated patch.

From the viewpoint of more notably exhibiting the effect of the invention, the medicinal agent is preferably produced from an acid addition salt of varenicline. The varenicline acid addition salt is preferably a hydrochloride, acetic acid salt, sulfuric acid salt, maleic acid salt, oxalic acid salt, citric acid salt, hydroiodic acid salt, hydrobromic acid salt, mesylic acid salt, tartaric acid salt or succinic acid salt of varenicline or a pharmaceutically acceptable salt of varenicline.

The medicated patch of the invention preferably further comprises a salt. The salt contains a substance, or its constituent component, that can bond with the medicinal agent to form a medicinal agent salt, and the salt content is no greater than the number of moles of the substance or its constituent component that bonds with the medicinal agent to form the medicinal agent salt, when a medicinal agent salt has been formed with the same number of moles as the medicinal agent in the medicated patch.

An example of the salt will now be explained. If the medicinal agent is represented as "A", the substance that can bond with the medicinal agent "A" to form the medicinal agent acid addition salt is represented as "HX" and the medicinal agent acid addition salt is represented as "A·HX", then the neutralization reaction can be represented by A·X+MOH→A+MX+H$_2$O, where the salt produced by the neutralization reaction is "MX". The salt in the medicated patch of the invention is "MX" in this example, and it contains the constituent component "X" of the substance that can bond with the medicinal agent "A" to form the medicinal agent salt "FIX". The content of "MX" is no greater than the number of moles of "HX" in "A·HX".

The salt may be produced during production of the medicated patch described above, or it may produced in the medicated patch after production (that is, during the storage after production and before use).

The salt is preferably at least one salt selected from the group consisting of metal chlorides, metal bromides, metal iodides, organic acid metal salts and ammonium salts, and more preferably it is at least one salt selected from the group consisting of sodium chloride, calcium chloride, aluminum chloride, stannous chloride, ferric chloride, magnesium chloride, potassium chloride, sodium citrate, sodium oxalate, sodium tartrate, sodium bromide and sodium succinate.

The medicated patch of the invention preferably further comprises an adsorbent. The adsorbent is an inorganic and/or organic material substance that adsorbs the polar solvent in the medicated patch, i.e. a polar solvent such as water produced and accumulated in the medicated patch during the neutralization reaction, or water used and accumulated in the medicated patch during the production process, methanol, ethanol or the like.

The present inventors have found that when a medicinal agent free form and metal salt (sodium chloride or the like) are formed by neutralization reaction of the acid addition salt of the medicinal agent, and the metal salt is neutralized together with an adhesive base material without removal by filtration treatment, for application of a more convenient production method, the metal salt generated by the neutralization reaction can undergo crystal deposition, and the crystals aggregate and grow with time, thus undesirably affecting the medicated patch production efficiency, pharmaceutical stability and pharmaceutical properties.

The present inventors have also found that salts derived from medicinal agent acid addition salts produced after neutralization reaction can undergo aggregation and growth centered on trace residues of the polar solvent (such as water, methanol or ethanol) used for production of the medicated patch and for the neutralization reaction, and that such aggregation and growth can be inhibited by including an adsorbent in the pressure-sensitive adhesive layer.

Since a medicated patch further comprising the aforementioned adsorbent has the salt type and content limited as explained above and also includes an adsorbent that adsorbs the polar solvent, the aggregation and growth of produced salts with time can be inhibited even when the medicinal agent salt is neutralized to produce the medicated patch, and this improves the medicated patch production efficiency, pharmaceutical stability and pharmaceutical properties.

For high adsorption power for the polar solvent in the medicated patch, the adsorbent is preferably at least one adsorbent selected from the group consisting of talc, kaolin, bentonite, hydrous silica, fumed silica, polyvinylpyrrolidone, propylene glycol, aminoalkyl methacrylate copolymer, crospovidone, carboxyvinyl polymer, lactic acid, acetic acid, zinc oxide, dextrin and dry aluminum hydroxide gel.

The medicated patch of the invention may be applied directly onto the skin as a "salve", or a pressure-sensitive adhesive layer may be formed on a support and the medicated patch included in the pressure-sensitive adhesive layer for application as a plaster or the like.

Effect of the Invention

According to the invention it is possible to provide a medicated patch comprising varenicline or a pharmaceutically acceptable salt of varenicline as the medicinal agent, having high cutaneous permeability for the medicinal agent, and having excellent pharmaceutical stability.

EXPLANATION OF SYMBOLS

1: Medicated patch, 2: support, 3: pressure-sensitive adhesive layer, 4: release sheet.

BEST MODES FOR CARRYING OUT THE INVENTION

Preferred embodiments will now be explained in detail, with reference to the accompanying drawings. Also, some of the drawings are exaggerated in size for easier illustration, and the dimensional proportions will not necessarily match those in the explanation.

Figure 1:
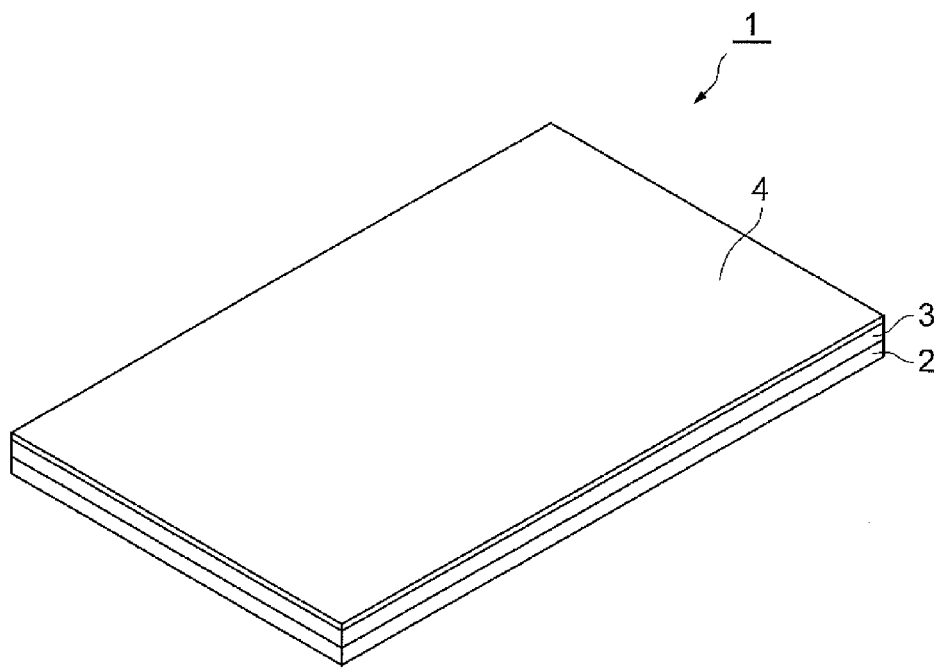
FIG. 1 is a perspective view of a preferred embodiment of the medicated patch of the invention.
Figure 2:
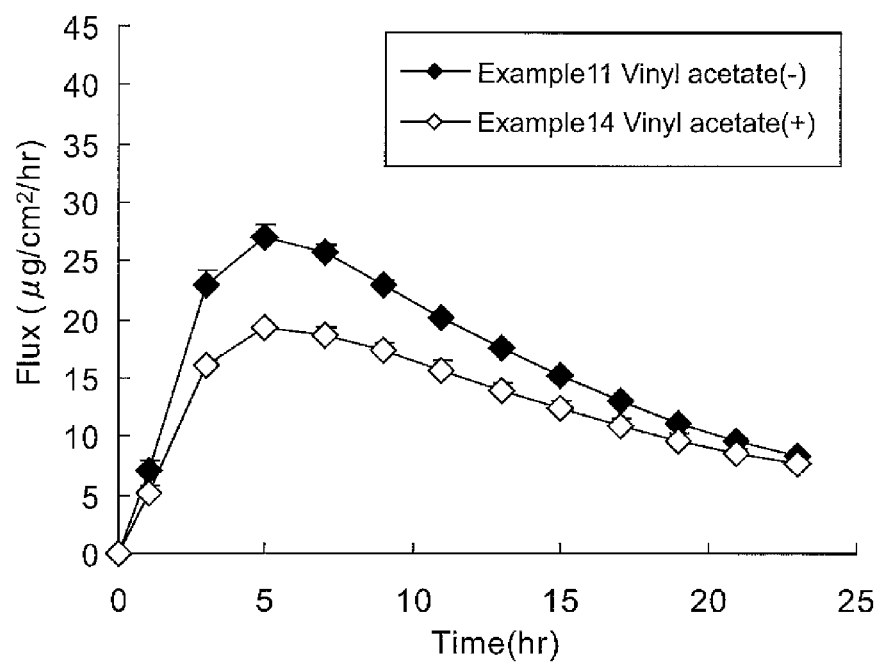
FIG. 2 is graph showing the effect on mouse cutaneous permeability by the presence or absence of a vinyl acetate-derived unit structure in an adhesive base material without functional groups.
Figure 3:
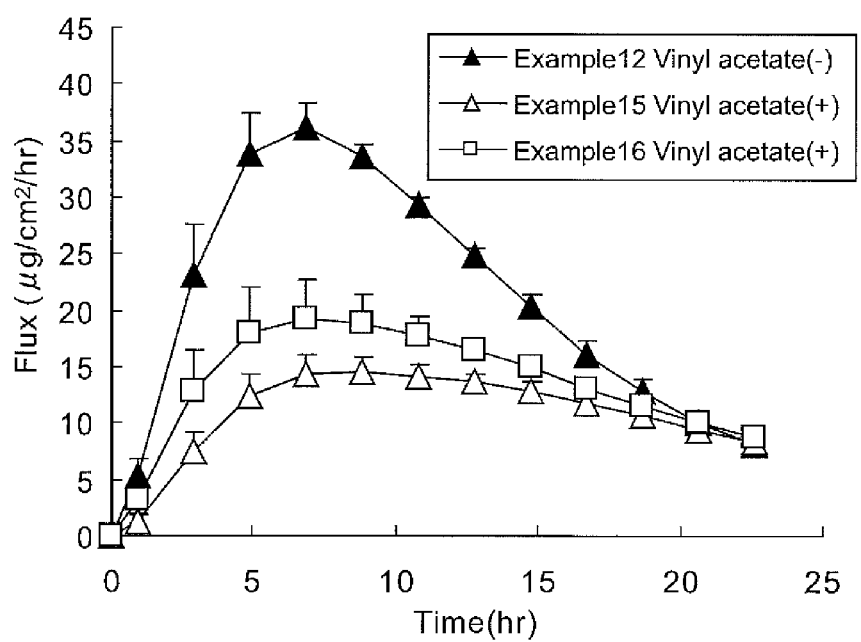
FIG. 3 is graph showing the effect on mouse cutaneous permeability by the presence or absence of a vinyl acetate-derived structural unit in an adhesive base material having a unit structure derived from a hydroxyl group-containing monomer.
Figure 4:
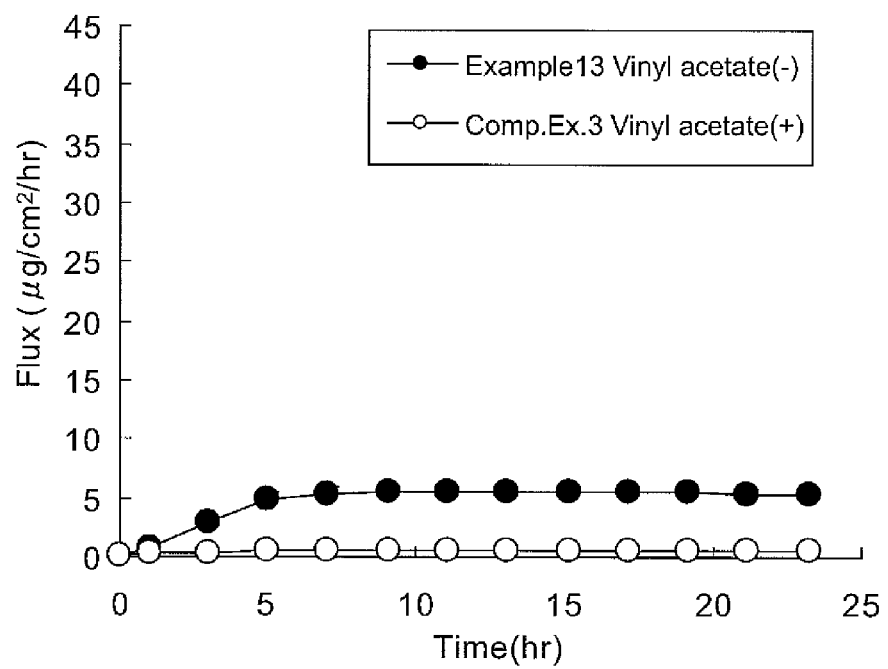
FIG. 4 is graph showing the effect on mouse cutaneous permeability by the presence or absence of a vinyl acetate-derived structural unit in an adhesive base material having a unit structure derived from a carboxyl group-containing monomer.
Figure 5:
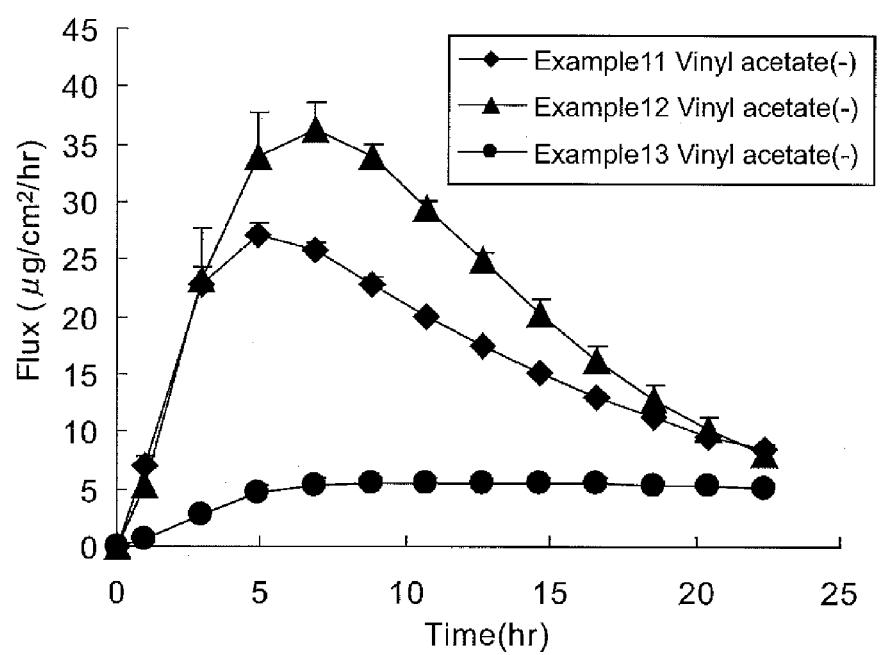
FIG. 5 is graph showing the effect on mouse cutaneous permeability by the type of functional group in the adhesive base material.
Figure 6:
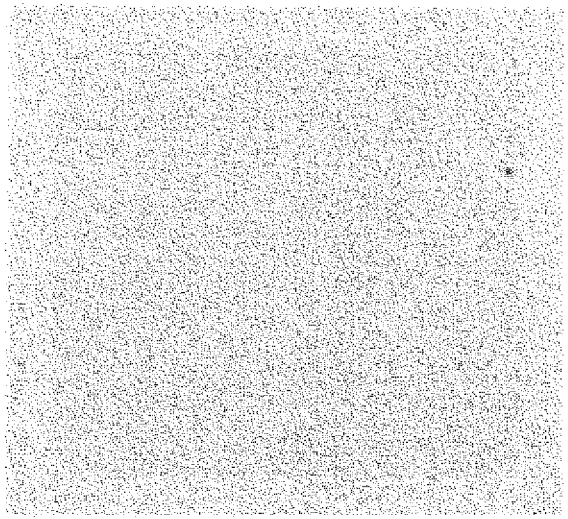
FIG. 6 is a photograph showing the degree of coloration of the medicated patch of Example 11.
Figure 7:
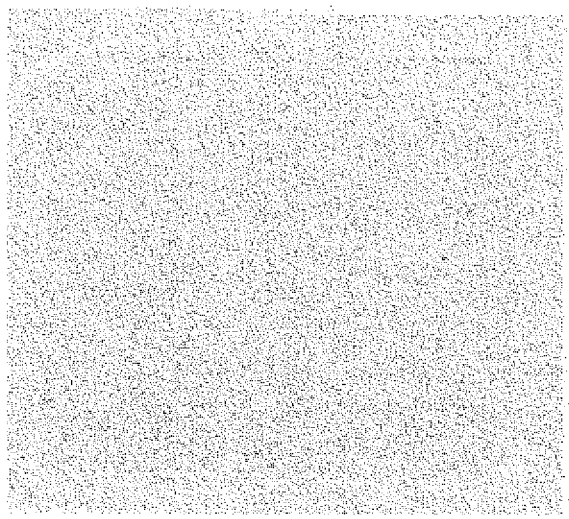
FIG. 7 is a photograph showing the degree of coloration of the medicated patch of Example 12.
Figure 8:
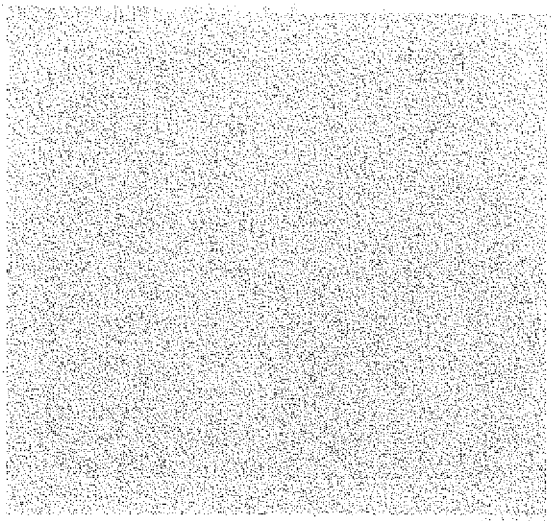
FIG. 8 is a photograph showing the degree of coloration of the medicated patch of Example 13.
Figure 9:
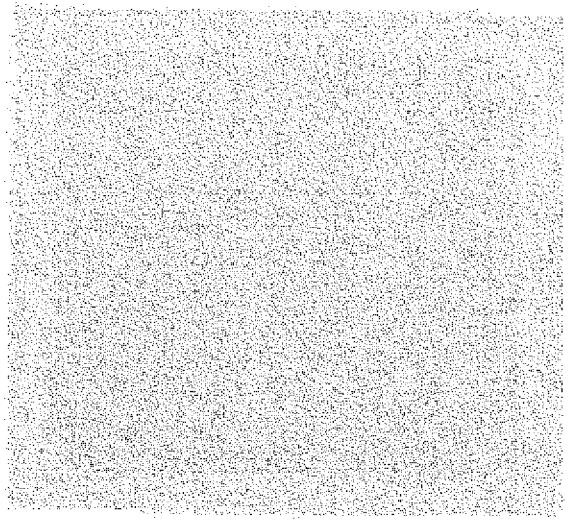
FIG. 9 is a photograph showing the degree of coloration of the medicated patch of Example 14.
Figure 10:
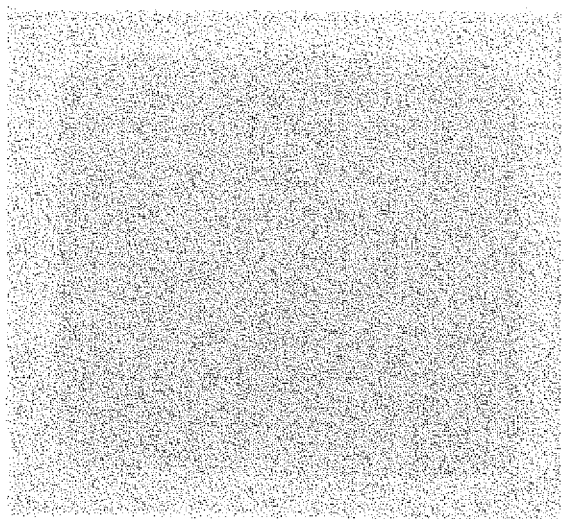
FIG. 10 is a photograph showing the degree of coloration of the medicated patch of Example 15.
Figure 11:
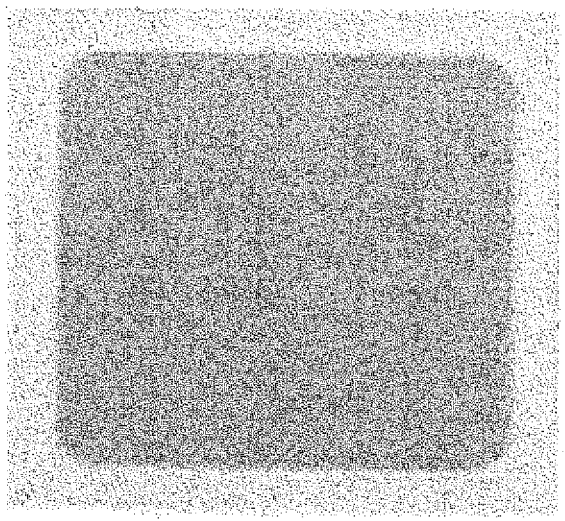
FIG. 11 is a photograph showing the degree of coloration of the medicated patch of Example 16.
Figure 12:
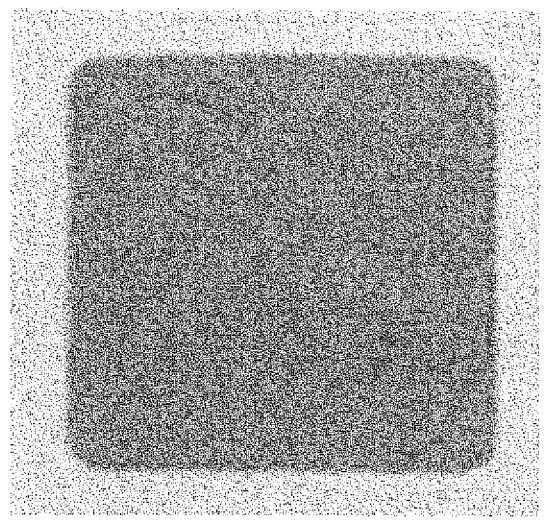
FIG. 12 is a photograph showing the degree of coloration of the medicated patch of Comparative Example 3.

FIG. 1 is a perspective view of a preferred embodiment of the medicated patch of the invention. In FIG. 1, the medicated patch 1 comprises a support 2, a pressure-sensitive adhesive layer 3 laminated on the support 2, and a release sheet 4 attached to the pressure-sensitive adhesive layer 3. The pressure-sensitive adhesive layer 3 is a medicated patch comprising a medicinal agent and an adhesive base material and having an acid value of no greater than 28, wherein the medicinal agent is varenicline or a pharmaceutically acceptable salt of varenicline.

The pressure-sensitive adhesive layer 3 may consist of two or more laminated layers, and it may be laminated on both sides instead of only one side of the support 2. The release sheet 4 is peeled off before attachment for use.

The material of the support 2 is not particularly restricted so long as it can generally be used in a medicated patch, and it may be elastic or non-elastic. Specifically, there may be used a film or sheet formed of a synthetic resin such as polyethylene terephthalate, polyethylene, polypropylene, polybutadiene, ethylenevinyl acetate polymer, polyvinyl chloride, polyester, nylon or polyurethane, or a laminated body, porous membrane, foam, woven fabric or nonwoven fabric thereof, or a paper material.

The pressure-sensitive adhesive layer 3 contains an adhesive base material. The adhesive base material may serve as the base of the pressure-sensitive adhesive layer 3 and is not particularly restricted so long as the acid value of the medicated patch is no greater than 28, but it is preferably an acrylic-based polymer. As acrylic-based polymers there may be suitably used homopolymers or copolymers of (meth)acrylic acid esters, or copolymers of alkyl (meth)acrylate esters and other monomers. The term "(meth)acrylic" includes "acrylic" and "methacrylic". As (meth)acrylic acid esters and alkyl (meth)acrylate esters there may suitably used (meth)acrylic acid esters of alkyl alcohols or alkyldiols. Preferred are C4-16 alkyl alcohols and alkyldiols. As other monomers there may be suitably used monomers having no carboxyl groups and having glass transition temperatures of at least room temperature (25° C.) when polymerized with the monomers alone. Examples of such monomers include styrene, methylstyrene, N-vinylpyrrolidone and (meth)acrylamide. An adhesive base material having such a structure can adequately inhibit decomposition of the medicinal agent by the adhesive base material, to prevent coloration of the medicated patch while also obtaining a high pharmaceutical property.

The acrylic-based polymer is not particularly restricted so long as the acid value of the medicated patch is no greater than 28, but it preferably contains no carboxyl groups. Such an acrylic-based polymer will allow the acid value to be easily reduced below the prescribed value, so that the pharmaceutical stability can be even further improved. The acrylic-based polymer also preferably has a hydroxyl group. Such an acrylic-based polymer can further improve the tissue permeability (cutaneous permeability) of the medicinal agent. The acrylic-based polymer also preferably contains no vinyl acetate as a monomer unit. Such an acrylic-based polymer can further inhibit decomposition of the medicinal agent in the medicated patch, and prevent coloration of the medicated patch.

Examples of acrylic-based polymers with no carboxyl groups include DURO-TAK900A, DURO-TAK2510, DURO-TAK4098, DURO-TAK2287 and DURO-TAK2516 (Henkel Japan, Ltd.). Examples of acrylic-based polymers containing no vinyl acetate as monomer units include DURO-TAK900A, DURO-TAK2510 and DURO-TAK2100 (Henkel Japan, Ltd.). Examples of acrylic-based polymers containing hydroxyl groups include DURO-TAK2510A, DURO-TAK2287 and DURO-TAK2516 (Henkel Japan, Ltd.).

Such adhesive base materials may be used alone or in combinations of two or more. The content of the adhesive base material is preferably 10-99 wt %, more preferably 15-90 wt % and most preferably 20-85 wt % based on the total weight of the pressure-sensitive adhesive layer 3, in consideration of formation of the pressure-sensitive adhesive layer 3 and tissue permeability of the active ingredient.

The type and content of the adhesive base material is preferably selected so that the pressure-sensitive adhesive layer 3 has an adhesive property. The phrase "has an adhesive property" means that it "exhibits a 1 second creep compliance larger than $1 \times 10^{-6}$ cm$^2$/dyne" at the applied temperature (for example, 30° C.-40° C.) (see Handbook of Pressure-sensitive Adhesive Technology, Edited by D. Satas, pg. 172, (1989)).

The pressure-sensitive adhesive layer 3 comprises varenicline or a pharmaceutically acceptable salt of varenicline, as a medicinal agent. The medicinal agent contains the free form of the medicinal agent salt obtained from the neutralization reaction, and the salt form remaining from incomplete neutralization.

Two or more of these medicinal agents may be used in combination if necessary, if this does not present an inconvenience by interaction. From the viewpoint of obtaining a sufficient drug effect as a medicated patch and in consideration of the physical properties and tissue absorption of the preparation, the content is preferably 0.5-50 wt % and most preferably 1-30 wt % based on the total weight of the pressure-sensitive adhesive layer 3.

From the viewpoint of storage stability before production, the medicinal agent is more preferably a medicinal agent produced from an acid addition salt. Examples of acid addition salt forms include hydrochlorides, acetic acid salts, sulfuric acid salts, maleic acid salts, oxalic acid salts, citric acid salts, hydroiodic acid salts, hydrobromic acid salts, mesylic acid salts, tartaric acid salts and succinic acid salts.

When an acid addition salt of the medicinal agent is used as the starting material in the pressure-sensitive adhesive layer 3, preferably neutralization reaction occurs with the medicinal agent acid addition salt by admixture with a neutralizer, to add the free base form of the medicinal agent which has higher cutaneous permeability.

The type of salt produced by the neutralization reaction (desalting reaction) is determined by the medicinal agent salt and the neutralizer used for neutralization. A metal salt is preferred as the salt produced by the neutralization reaction. The salt produced when the acid addition salt of the medicinal agent is neutralized is preferably at least one selected from the group consisting of metal chlorides, metal bromides, metal iodides, organic acid metal salts and ammonium salts, and among these it is preferably at least one type selected from sodium chloride, calcium chloride, aluminum chloride, stannous chloride, ferric chloride, magnesium chloride, potassium chloride, sodium citrate, sodium oxalate, sodium tartrate, sodium bromide and sodium succinate.

The neutralizer used for the neutralization reaction is not particularly restricted, but when a medicinal agent produced from an acid addition salt is used as the medicinal agent, a basic substance is suitable, while from the viewpoint of complete desalting of the medicinal agent acid addition salt, a strong base is suitable and an alkali metal hydroxide is especially preferred. Specific examples of neutralizers include sodium hydroxide, potassium hydroxide and magnesium hydroxide, among which sodium hydroxide is especially preferred. The neutralizer is added to convert all or a portion of the basic medicinal agent to a free base (free form). In order to avoid decomposing the medicinal agent by excess neutralizer, the neutralizer is preferably added in a range of 0.5-4 equivalents and more preferably in a range of 0.5-1 equivalents with respect to the acid-base equivalents of the medicinal agent. The addition may be all at once or divided in several doses during the production process.

The medicated patch 1 produced by the neutralization reaction comprises a salt produced by neutralization in the pressure-sensitive adhesive layer 3.

The salt in the pressure-sensitive adhesive layer 3 will tend to undergo aggregation and growth centered on trace residues of the polar solvent (such as water, methanol or ethanol) used for production of the medicated patch or for the neutralization reaction, but aggregation and growth of the salt is inhibited by including an adsorbent in the pressure-sensitive adhesive layer 3. Adding an adsorbent can ensure uniform dispersion of the crystals. This will improve the production efficiency, pharmaceutical stability and pharmaceutical properties of the medicated patch 1.

An adsorbent is therefore preferably added when the pressure-sensitive adhesive layer 3 contains a salt in the composition. Suitable adsorbents include the inorganic materials and organic materials mentioned as having hygroscopicity, moisture proofness and adsorption properties among the additives mentioned in "Dictionary of Drug Additives 2000, Apr. 28, 2000, First Printing", as well as aminoalkyl methacrylate copolymers and zinc oxide, which are not mentioned in "Dictionary of Drug Additives 2000" but are known to have adsorption properties. Of these there are preferred minerals such as talc, kaolin and bentonite; silicon compounds such as fumed silica (AEROSIL® and the like) and hydrous silica; metal compounds such as zinc oxide and dry aluminum hydroxide gel; weak acids such as lactic acid and acetic acid; sugars such as dextrin; and high molecular polymers such as polyvinylpyrrolidone, propylene glycol, aminoalkyl methacrylate copolymer, crospovidone and carboxyvinyl polymer, which may also be used in combinations of two or more if necessary.

The content of the adsorbent in the pressure-sensitive adhesive layer 3 is preferably 0.5-50 wt % based on the total weight of the pressure-sensitive adhesive layer 3. At 0.5 wt % or lower, it may not be possible to obtain a sufficient effect of inhibiting aggregation and growth of the salt crystals and uniformly dispersing the crystals. At above 50 wt %, the pressure-sensitive adhesive force of the pressure-sensitive adhesive layer 3 will tend to be reduced, thus hampering attachment.

An acetic acid and/or acetic acid salt is preferably contained in the medicated patch, of which all or a portion of the medicinal agent is essentially a varenicline free base. A medicated patch that contains acetic acid and/or an acetic acid salt is resistant to decomposition of the medicinal agent with time and has excellent content stability.

The medicated patch 1 of the invention may also contain a tackifier, plasticizer, absorption accelerator, antioxidant, filler, crosslinking agent, preservative or ultraviolet absorber as necessary, in addition to the composition described above.

Examples of tackifiers include rosin-based resins such as ESTER GUM (trade name of Arakawa Chemical Industries, Ltd.), HARIESTER (trade name of Harima Chemicals, Inc.), PENTALYN (trade name of Eastman Chemical Company) and FORAL (trade name of Eastman Chemical Company); terpene-based resins such as YS Resin (trade name of Yasuhara Chemical Co., Ltd.) and Piccolyte (trade name of Loos & Dilworth, Inc.), petroleum resins such as ARKON (trade name of Arakawa Chemical Industries, Ltd.), REGALREZ (trade name of Eastman Chemical Company), PICCOLASTIC (trade name of Eastman Chemical Company), ESCOREZ (trade name of Exxon Corp.), WINGTACK (trade name of Goodyear) and QUINTONE (trade name of Zeon Corp.), and phenol-based resins, xylene-based resins and the like.

These tackifiers may be used as single types alone, or two or more thereof may be used in combination. The content of the tackifier is preferably 10-90 wt %, more preferably 15-70 wt % and most preferably 20-60 wt % based on the total weight of the pressure-sensitive adhesive layer 3, in consideration of sufficient pressure-sensitive adhesive force of the medicated patch 1 and low local irritation during peeling.

Examples of plasticizers include petroleum-based oils such as paraffin-based process oils, naphthene-based process oils and aromatic-based process oils; squalane and squalene; plant-based oils such as olive oil, camellia oil, castor oil, tall oil and peanut oil; dibasic acid esters such as dibutyl phthalate and dioctyl phthalate; liquid rubbers such as polybutene and liquid isoprene rubber; and diethylene glycol, polyethylene glycol, propylene glycol, dipropylene glycol and the like. Any of these may be used alone or in combinations of two or more.

Liquid paraffin and liquid polybutene are especially preferred for use for this embodiment.

The content of the plasticizer in the pressure-sensitive adhesive layer 3 is preferably 1-60 wt %, more preferably 2-50 wt % and most preferably 3-40 wt % based on the total weight of the pressure-sensitive adhesive layer 3, in consideration of maintaining sufficient pressure-sensitive adhesive force as a medicated patch 1.

As absorption accelerators there may be suitably used aliphatic alcohols such as isostearyl alcohol, fatty acids such as capric acid, fatty acid derivatives such as propyleneglycol monolaurate and isopropyl myristate, and propylene glycol, polyethylene glycol, diethanolamine laurate and the like. These absorption accelerators may be used alone or in combinations of two or more. The content of the absorption accelerator is preferably 1-30 wt %, more preferably 3-20 wt % and most preferably 5-15 wt % based on the total weight of the medicated patch 1, in consideration of obtaining sufficient permeability and low local irritation of the active ingredient with respect to tissue, for the obtained patch.

Examples of fillers include aluminum hydroxide, calcium carbonate, magnesium carbonate; silicic acid salts such as aluminum silicate and magnesium silicate; and silicic acid, barium sulfate, calcium sulfate, calcium zincate, zinc oxide, titanium oxide and the like.

Examples of ultraviolet absorbers include p-aminobenzoic acid derivatives, anthranilic acid derivatives, salicylic acid derivatives, coumarin derivatives, amino acid-based compounds, imidazoline derivatives, pyrimidine derivatives, dioxane derivatives and the like.

These antioxidants, fillers, crosslinking agents, preservatives and ultraviolet absorbers may be added to a total of preferably no greater than 5 wt %, even more preferably no greater than 3 wt % and most preferably no greater than 1 wt %, based on the total weight of the pressure-sensitive adhesive layer 3.

An example of a method for producing the medicated patch 1 of this embodiment will now be explained.

First, a mixture for formation of the pressure-sensitive adhesive layer 3 is prepared. A mixer is used to dissolve or disperse the adhesive base material, medicinal agent acid addition salt, neutralizer, adsorbent and other components in the solvent for the adhesive base material, to obtain a mixture for formation of the pressure-sensitive adhesive layer 3.

The solvent for the adhesive base material may be toluene, hexane, ethyl acetate, cyclohexane, heptane, butyl acetate, ethanol, methanol, xylene, isopropanol or the like. These are appropriately selected according to the components to be dissolved or dispersed, and one may be used alone or a combination of two or more used together.

Next, the obtained mixture for formation of the pressure-sensitive adhesive layer 3 is spread directly onto a support 2 to form a pressure-sensitive adhesive layer 3, or it is spread onto a release-treated paper sheet or film to form the pressure-sensitive adhesive layer 3 and the support 2 situated thereover for contact transfer of the pressure-sensitive adhesive layer 3 onto the support 2. Next, a release sheet 4 for protection of the pressure-sensitive adhesive layer 3 is attached to the pressure-sensitive adhesive layer 3 to obtain a medicated patch 1.

When it is to be stored inside a package, the produced medicated patch 1 is preferably stored in the presence of a storage stabilizer. As storage stabilizers there may be used desiccants, deoxidizers and the like, and examples of common materials as desiccants include any substances with the capacity of physical or chemical adsorption, among which there may be mentioned zeolite, silica gel, alumina, molecular sieves and montmorillonite. Specifically, there may be mentioned Sorb-It (Absorbents & Desiccants Corporation of America) and PharmaKeep (Mitsubishi Gas Chemical Co. Inc.). The deoxidizer used for the invention is not particularly restricted so long as it can absorb, adsorb or remove oxygen. Various known deoxidizers can also be used. Examples include active iron oxide, hydrosulfite, butylhydroxytoluene and the like, in powdered, granular or tablet form. Commercial products include AGELESS (Mitsubishi Gas Chemical Co., Inc.) and VITALON (Toagosei Co., Ltd.).

EXAMPLES

The present invention will now be explained in detail by examples, with the understanding that the invention is not limited thereto, and various modifications may be made that are within the technical concept of the invention. The "%" values throughout the examples all signify wt %.

Example 1

A mixer was used to premix varenicline tartrate, sodium hydroxide, crospovidone and methanol (solvent), and then a base material (A) (acrylic adhesive base material without a functional group in the monomer) was added and mixed therewith to obtain a pressure-sensitive adhesive solution. This was spread onto a release-treated film, the solvent was removed by drying to form a pressure-sensitive adhesive layer, and then a support was placed thereover and the pressure-sensitive adhesive layer was contact transferred to obtain a medicated patch. Table 1 shows the contents for each of Examples 1-3 and Comparative Example 1.

Examples 2 and 3

Medicated patches for Examples 2 and 3 were obtained in the same manner as Example 1, except that the bases used were base material (B) (acrylic adhesive base material with a hydroxyl group in the monomer) and base material (C) (acrylic adhesive base material with a carboxyl group in the monomer, instead of base material (A).

Comparative Example 1

A medicated patch for Comparative Example 1 was obtained in the same manner as Example 1, except that base material (D) (acrylic adhesive base material with a carboxyl group in the monomer) was used instead of base material (A).

(Measurement of Acid Value)

The acid value was measured for the medicated patches of Examples 1-3 and Comparative Example 1. The results are shown in Table 2. The acid value was measured by the following procedure, as the acid value for Examples 1-3 and Comparative Example 1 according to the definition of acid value in the Japanese Pharmacopeia. A tetrahydrofuran/methanol/water mixture was added to the pressure-sensitive adhesive layer 1, and subjected to ultrasonic treatment to produce a uniform dispersion. A potassium hydroxide (hereunder abbreviated as KOH) aqueous solution was added dropwise to the solution and the pH was measured with a glass electrode/reference electrode. The neutralization point is the center point (point of inflection) where the pH changes abruptly, and when multiple points of inflection exist, the neutralization point is the point of inflection of highest pH. The dropwise addition amount calculated in the same manner with the solvent alone was subtracted as blank from the dropwise addition amount up to the neutralization point and considered the actual necessary amount of KOH, and the acid value was calculated from formula (1).

[Formula 2]

$$\text{Acid value} = [56.11 \text{ (g/mol)} \times \text{amount of potassium hydroxide necessary for neutralization (mol)}] / \text{medicated patch weight 100 (mg)} \quad (1)$$

(In vitro Hairless Mouse Skin Permeation Test)

Skin was peeled from the back of a hairless mouse and was fitted in a flow-through cell (5 cm$^2$) with the dermis side on the receptor layer side, and with exterior circulation of hot water set so that the skin surface temperature was 32° C. The patches of Examples 1-3 and Comparative Example 1 were each attached to the stratum corneum side, and phosphate-buffered saline at pH 7.4 was used on the receptor layer for sampling up to 24 hours every 120 minutes, at a rate of 5 mL/hr. The flow rate of the obtained receptor solution was measured precisely every hour, and the medicinal agent concentration was measured by high performance liquid chromatography (HPLC). The permeation rate per hour was calculated from the measured values for the flow rate and medicinal agent concentration, and the maximum skin permeation rate (maximum flux) was determined for each example. The results are shown in Table 2.

TABLE 1

|  |  | Example 1 | Example 2 | Example 3 | Comp. Ex. 1 |
|---|---|---|---|---|---|
| Varenicline tartrate | | 10.0 | 10.0 | 10.0 | 10.0 |
| Sodium hydroxide | | 2.2 | 2.2 | 2.2 | 2.2 |
| Crospovidone | | 3.0 | 3.0 | 3.0 | 3.0 |
| Base material | Base material (A) | 85.8 | — | — | — |
|  | Base material (B) | — | 85.8 | — | — |
|  | Base material (C) | — | — | 85.8 | — |
|  | Base material (D) | — | — | — | 85.8 |

(Units: parts by weight)

TABLE 2

|  | Example 1 | Example 2 | Example 3 | Comp. Ex. 1 |
|---|---|---|---|---|
| Acid value | 0.6 | 0.0 | 20.8 | 34.8 |
| Maximum FLUX (μg/cm$^2$/hr) | 22.5 | 34.1 | 6.8 | 0.3 |

Example 4

An organic solvent was added to and mixed with varenicline tartrate, sodium hydroxide, crospovidone and an acrylic adhesive base material (DURO-TAK 387-2510 by Henkel Japan, Ltd.), to obtain a uniform coating solution. This was spread onto a release-treated film, the solvent was removed by drying to form a pressure-sensitive adhesive layer, and then a support was placed thereover and the pressure-sensitive adhesive layer was contact transferred to obtain a medicated patch. The contents are shown in Table 3.

Examples 5-8

Medicated patches were obtained for Examples 5-8 in the same manner as Example 4, except that the basic substances used were potassium hydroxide, sodium acetate, sodium carbonate and triethanolamine, instead of sodium hydroxide. The contents are shown in Table 3.

Comparative Example 2

A medicated patch was produced in the same manner as Example 1, except that no basic substance was added. The contents are shown in Table 3.

The acid value and maximum flux values were determined for the medicated patches of Examples 4-8 and Comparative Example 2, by the same method as Example 1. The pH of each patch was measured by the following method. The results are shown in Table 4.

(Patch pH Measurement Test)

The release sheet was removed from the medicated patch and a portion for 20 mg of the pressure-sensitive adhesive layer weight was used as a sample. After adding 20 mL of water to the sample, irradiating it with ultrasonic waves for 6 hours and then shaking for 3 hours, the pH of the obtained solution was measured with a pH meter comprising a glass electrode/reference electrode.

Examples 9 and 10

Medicated patches for Examples 9 and 10 were obtained in the same manner as Example 4 (2.0 equivalents), except that the amounts of sodium hydroxide were 1.6 and 1.2 equivalents with respect to the medicinal agent. Comparative Example 2 (0 equivalents) was used as the control. The contents are shown in Table 5, and the patch pH and maximum flux values measured in the same manner as Example 4 are shown in Table 6.

TABLE 5

|  | Example 4 | Example 9 | Example 10 | Comp. Ex. 2 |
| --- | --- | --- | --- | --- |
| Varenicline tartrate | 10.0 | 10.0 | 10.0 | 10.0 |
| Sodium hydroxide | 2.2 (2.0 equiv) | 1.8 (1.6 equiv) | 1.3 (1.2 equiv) | — |
| Crospovidone | 3.0 | 3.0 | 3.0 | 3.0 |
| DURO-TAK 387-2510 | 84.8 | 85.2 | 85.7 | 87.0 |

(Units: parts by weight)

TABLE 6

|  | Example 4 | Example 9 | Example 10 | Comp. Ex. 2 |
| --- | --- | --- | --- | --- |
| Patch pH | 9.27 | 8.75 | 8.43 | 4.79 |
| Maximum FLUX($\mu g/cm^2/hr$) | 35.4 | 12.4 | 8.5 | 0.1 |

Example 11

An organic solvent was added to and mixed with varenicline tartrate, sodium hydroxide, crospovidone and an acrylic adhesive base material (DURO-TAK 87-900A by Henkel Japan, Ltd.), to obtain a uniform coating solution. This was spread onto a release-treated film, the solvent was removed by drying to form a pressure-sensitive adhesive layer, and then a support was placed thereover and the pressure-sensitive adhe-

TABLE 3

|  |  | Example 4 | Example 5 | Example 6 | Example 7 | Example 8 | Comp. Ex. 2 |
| --- | --- | --- | --- | --- | --- | --- | --- |
| Varenicline tartrate |  | 10.0 | 10.0 | 10.0 | 10.0 | 10.0 | 10.0 |
| Basic sub-stance | Sodium hydroxide | 2.2 | — | — | — | — | — |
|  | Potassium hydroxide | — | 3.1 | — | — | — | — |
|  | Sodium acetate | — | — | 4.5 | — | — | — |
|  | Sodium carbonate | — | — | — | 2.9 | — | — |
|  | Triethanolamine | — | — | — | — | 8.3 | — |
| Crospovidone |  | 3.0 | 3.0 | 3.0 | 3.0 | 3.0 | 3.0 |
| DURO-TAK 387-2510 |  | 84.8 | 83.9 | 82.5 | 84.1 | 78.7 | 87.0 |

(Units: parts by weight)

TABLE 4

|  | Example 4 | Example 5 | Example 6 | Example 7 | Example 8 | Comp. Ex. 2 |
| --- | --- | --- | --- | --- | --- | --- |
| Acid value | 0.0 | 0.6 | 6.7 | 6.2 | 20.8 | 29.7 |
| Patch pH | 9.27 | 9.09 | 8.78 | 7.66 | 7.81 | 4.79 |
| Maximum FLUX($\mu g/cm^2/hr$) | 35.4 | 21.2 | 11.9 | 7.5 | 5.0 | 0.1 | sive layer was contact transferred to obtain a medicated patch. Table 7 shows the contents for each of Examples 11-16 and Comparative Example 3. In Table 7, "(None)" indicates that the monomer in the adhesive base material contained essentially no functional groups, "(—OH)" indicates that the monomer in the adhesive base material contained hydroxyl groups, and "(—COOH)" indicates that the monomer in the adhesive base material contained carboxyl groups.

Example 12

A medicated patch (using DURO-TAK 387-2510 as the base material) was obtained in the same manner as Example 4.

Examples 13-16

Medicated patches for Examples 10-14 were obtained in the same manner as Example 8, except that DURO-TAK 87-2100, DURO-TAK 87-4098, DURO-TAK 87-2287, DURO-TAK 87-2516 and DURO-TAK 87-2196 (all products of Henkel Japan, Ltd.) were used instead of DURO-TAK 87-900A as the base materials.

The acid values were measured for the medicated patches of Examples 11-13 and Comparative Example 3, by the same method as Example 4. Also, the maximum flux and patch pH values were measured for the medicated patches of Examples 11-16 and Comparative Example 3, by the same method as Example 4. The medicinal agent content in the plaster weight and the patch coloration were measured by the following methods. The results are shown in Table 8. The transmission profiles in the hairless mouse skin permeation test are shown in FIGS. 2 to 5. In the graphs, "Vinyl acetate (+)" indicates that the adhesive base material had a unit structure derived from vinyl acetate monomer, and "vinyl acetate (−)" indicates that the adhesive base material had essentially no unit structure derived from vinyl acetate monomer. FIGS. 6 to 12 show the degree of coloration for the medicated patches of Examples 11-16 and Comparative Example 3, as concrete examples of coloration evaluation results.

(Medicinal Agent Content Test)

The varenicline in each of the obtained medicated patches was extracted by addition of tetrahydrofuran and methanol, shaking and ultrasonic treatment, and the medicinal agent content for each single patch was measured by HPLC. The results are shown as medicinal agent content (%) of the plaster weight.

(Patch Coloration)

The degree of coloration of each obtained medicated patch after its preparation was evaluated based on the following scale:

A: Virtually no coloration (faint yellow)
B: Some coloration (faint yellow-yellow)
C: Strong coloration (orange-brown).

TABLE 7

|  |  | Example 11 | Example 12 | Example 13 | Example 14 | Example 15 | Example 16 | Comp. Ex. 3 |
|---|---|---|---|---|---|---|---|---|
| Varenicline tartrate | | 10.0 | 10.0 | 10.0 | 10.0 | 10.0 | 10.0 | 10.0 |
| Sodium hydroxide | | 2.2 | 2.2 | 2.2 | 2.2 | 2.2 | 2.2 | 2.2 |
| Crospovidone | | 3.0 | 3.0 | 3.0 | 3.0 | 3.0 | 3.0 | 3.0 |
| Pressure-sensitive adhesive | DURO-TAK 87-900A | 85.8 (None) | — | — | — | — | — | — |
| | DURO-TAK 387-2510 | — | 85.8 (—OH) | — | — | — | — | — |
| | DURO-TAK 87-2100 | — | — | 85.8 (—COOH) | — | — | — | — |
| | DURO-TAK 87-4098 | — | — | — | 85.8 (None) | — | — | — |
| | DURO-TAK 87-2287 | — | — | — | — | 85.8 (—OH) | — | — |
| | DURO-TAK 87-2516 | — | — | — | — | — | 85.8 (—OH) | — |
| | DURO-TAK 87-2196 | — | — | — | — | — | — | 85.8 (—COOH) |

(Units: parts by weight)

TABLE 8

|  | Example 11 | Example 12 | Example 13 | Example 14 | Example 15 | Example 16 | Comp. Ex. 3 |
|---|---|---|---|---|---|---|---|
| Acid value | 0.6 | 0.0 | 20.8 | — | — | — | 34.8 |
| Content in plaster (%) | 99.8 | 99.5 | 94.6 | 79.8 | 65.5 | 78.2 | 80.5 |
| Patch coloration evaluation | A | A | A | A | B | C | C |
| Maximum FLUX ($\mu g/cm^2/hr$) | 27.0 | 36.3 | 5.5 | 19.3 | 14.7 | 19.3 | 0.5 |

Example 17

A mixer was used to premix varenicline tartrate, sodium hydroxide and liquid paraffin, and then DURO-TAK 87-900A and a separately prepared mixed solution comprising SIS (styrene-isoprene-styrene block copolymer), alicyclic hydrocarbon resin and toluene (solvent) was added thereto and mixed therewith to obtain a pressure-sensitive adhesive solution. This was spread onto a release-treated film, the solvent was removed by drying to form a pressure-sensitive adhesive layer, and then a support was placed thereover and the pressure-sensitive adhesive layer was contact transferred to obtain a medicated patch. The contents and maximum flux values are shown in Table 9. The units of the values for the contents are parts by weight.

TABLE 9

|  |  | Example 17 |
|---|---|---|
| Varenicline tartrate |  | 10.0 |
| Sodium hydroxide |  | 2.2 |
| Crospovidone |  | 3.0 |
| Liquid paraffin |  | 18.1 |
| Base material and | DURO-TAK 87-900A | 34.9 |
| tackifying resin | SIS | 15.9 |
| Alicyclic hydrocarbon resin |  | 15.9 |
| Maximum FLUX ($\mu g/cm^2/hr$) |  | 32.5 |

Example 18

PharmaKeep (Mitsubishi Gas Chemical Co., Inc.) was enclosed as a preservative together with the medicated patch of Example 4 during its storage inside a package. PharmaKeep is a preservative with primarily a drying function and deoxidizing function, and the type used for this example was selected to keep the interior of the package at a humidity of 30%.

Example 19

The medicated patch was stored in the same manner as Example 18, except that Sorb-It (Adsorbents & Desiccants Corporation of America) was used as the preservative. Sorb-It is a preservative with a drying function which maintains a dry state inside packages.

Example 20

The medicated patch was stored in the same manner as Example 18, except that AGELESS (Mitsubishi Gas Chemical Co., Inc.) was used as the preservative. AGELESS is a preservative with a deoxidizing function, which maintains an oxygen concentration of no greater than 0.1% inside packages.

Example 21

The medicated patch was stored in the same manner as Example 18, except that no preservative was included.
(Content Stability Test)
For the medicated patches of Examples 18-21, the medicinal agent contents in the patches immediately after preparation of the patch (initial) and after 1 month of storage under conditions of 40° C., 75% humidity were measured by the medicinal agent content test described above. The results are shown in Table 10, as contents (%) with respect to the initial values. In Table 10, "+" indicates that the corresponding preservative was included, and "−" indicates that the corresponding preservative was not included.

TABLE 10

| Preservatives (function) | Example 18 | Example 19 | Example 20 | Example 21 |
|---|---|---|---|---|
| PharmaKeep (Drying, deoxidizing) | + | − | − | − |
| SORB-IT (Drying) | − | + | − | − |
| AGELESS (Deoxidizing) | − | − | + | − |
| Content (%: wrt initial) | 99.5 | 99.1 | 98.7 | 91.2 |

Example 22

A mixer was used for prior addition and mixing of an organic solvent with varenicline tartrate, sodium hydroxide, crospovidone, acetic acid, sodium acetate and an acrylic adhesive base material (DURO-TAK 387-2510 by Henkel Japan, Ltd.), and a uniform coating solution was obtained. This was spread onto a release-treated film, the solvent was removed by drying to form a pressure-sensitive adhesive layer, and then a support was placed thereover and the pressure-sensitive adhesive layer was contact transferred to obtain a medicated patch. The contents are shown in Table 11.

Example 23

A medicated patch was obtained in the same manner as Example 22, except that no acetic acid or sodium acetate was added, and the amount of sodium hydroxide added was 1.6 equivalents, which was below the desalting equivalent (2.0).

Example 24

A medicated patch (using DURO-TAK 387-2510 as the base material) was obtained in the same manner as Example 4.
(Content Stability Test)
For the medicated patches of Examples 22-24, the medicinal agent contents in the patches immediately after preparation of each patch (initial) and after 2 weeks of storage under conditions of 60° C., 75% humidity were measured by the medicinal agent content test described above. The results are shown in Table 11, as contents (%) with respect to the initial values.

TABLE 11

|  | Example 22 | Example 23 | Example 24 |
|---|---|---|---|
| Varenicline tartrate | 10.0 | 10.0 | 10.0 |
| Sodium hydroxide | 2.2 | 1.8 | 2.2 |
| Crospovidone | 3.0 | 3.0 | 3.0 |
| DURO-TAK 387-2510 | 82.8 | 85.2 | 84.8 |
| Acetic acid | 0.7 | — | — |
| Sodium acetate | 1.3 | — | — |
| Content (%: wrt initial) | 99.1 | 98.9 | 97.1 |

(Addition units: parts by weight)

INDUSTRIAL APPLICABILITY

According to the invention it is possible to provide a medicated patch comprising varenicline or a pharmaceutically acceptable salt of varenicline as the medicinal agent, having high cutaneous permeability for the medicinal agent, and having excellent pharmaceutical stability.

The invention claimed is:

1. A medicated patch comprising a support and a pressure-sensitive adhesive,
wherein the pressure-sensitive adhesive comprises a composition containing as a medicinal agent varenicline in its free base form, a metal salt, an adhesive base material and an adsorbent that adsorbs a polar solvent in the composition,
wherein varenicline in its free base form and the metal salt are produced by a neutralization reaction between a medicinal agent acid addition salt and a metal hydroxide, which is added in an amount to convert all or a portion of the medicinal agent to the free base form,
wherein the medicinal agent acid addition salt is selected from hydrochloride, acetic acid salt, sulfuric acid salt, maleic acid salt, oxalic acid salt, citric acid salt, hydroiodic acid salt, hydrobromic acid salt, mesylic acid salt, tartaric acid salt or succinic acid salt of the medicinal agent,
wherein the composition has a pH of 7.5 or greater, and
wherein the adhesive base material is an acrylic-based polymer containing no carboxyl groups and no vinyl acetate as a monomer unit.

2. The medicated patch according to claim 1, wherein the pH is 9.0 or greater.

3. The medicated patch according to claim 1, wherein the adhesive base material is an acrylic-based polymer with hydroxyl groups.

4. The medicated patch according to claim 1, wherein the metal salt contains a substance, or its constituent component, that can bond with the medicinal agent to form a medicinal agent salt, and the salt content is no greater than the number of moles of the substance or its constituent component that bonds with the medicinal agent to form the medicinal agent salt, when the medicinal agent salt has been formed with the same number of moles as the medicinal agent in the medicated patch.

5. The medicated patch according to claim 4, wherein the metal salt is produced in the medicated patch during or after production.

6. The medicated patch according to claim 4, wherein the metal salt is at least one salt selected from the group consisting of metal chlorides, metal bromides, metal iodides, organic acid metal salts, and ammonium salts.

7. The medicated patch according to claim 4, wherein the metal salt is at least one salt selected from the group consisting of sodium chloride, calcium chloride, aluminum chloride, stannous chloride, ferric chloride, magnesium chloride, potassium chloride, sodium citrate, sodium oxalate, sodium tartrate, sodium bromide, and sodium succinate.

8. The medicated patch according to claim 1, wherein the adsorbent is at least one adsorbent selected from the group consisting of talc, kaolin, bentonite, hydrous silica, fumed silica, polyvinylpyrrolidone, propylene glycol, aminoalkyl methacrylate copolymer, crospovidone, carboxyvinyl polymer, lactic acid, acetic acid, zinc oxide, dextrin, and dry aluminum hydroxide gel.

9. A method for improving tissue permeability of a medicinal agent of a medicated patch comprising varenicline or a pharmaceutically acceptable salt of varenicline as the medicinal agent, comprising:
providing a medicated patch comprising a support and a pressure-sensitive adhesive,
wherein the pressure-sensitive adhesive comprises a composition containing as a medicinal agent varenicline in its free base form, a metal salt, an adhesive base material and an adsorbent that adsorbs a polar solvent in the composition,
wherein varenicline in its free base form and the metal salt are produced by a neutralization reaction between a medicinal agent acid addition salt and a metal hydroxide, which is added in an amount to convert all or a portion of the medicinal agent to the free base form,
wherein the medicinal agent acid addition salt is selected from hydrochloride, acetic acid salt, sulfuric acid salt, maleic acid salt, oxalic acid salt, citric acid salt, hydroiodic acid salt, hydrobromic acid salt, mesylic acid salt, tartaric acid salt or succinic acid salt of the medicinal agent,
wherein the composition has a pH of 7.5 or greater, and
wherein the adhesive base material is an acrylic-based polymer containing no carboxyl groups and no vinyl acetate as a monomer unit.

10. A method for improving pharmaceutical stability of a medicated patch comprising varenicline or a pharmaceutically acceptable salt of varenicline, comprising:
providing a medicated patch comprising a support and a pressure-sensitive adhesive,
wherein the pressure-sensitive adhesive comprises a composition containing as a medicinal agent varenicline in its free base form, a metal salt, an adhesive base material and an adsorbent that adsorbs a polar solvent in the composition,
wherein varenicline in its free base form and the metal salt are produced by a neutralization reaction between a medicinal agent acid addition salt and a metal hydroxide, which is added in an amount to convert all or a portion of the medicinal agent to the free base form,
wherein the medicinal agent acid addition salt is selected from hydrochloride, acetic acid salt, sulfuric acid salt, maleic acid salt, oxalic acid salt, citric acid salt, hydroiodic acid salt, hydrobromic acid salt, mesylic acid salt, tartaric acid salt or succinic acid salt of the medicinal agent,
wherein the composition has a pH of 7.5 or greater, and
wherein the adhesive base material is an acrylic-based polymer containing no carboxyl groups and no vinyl acetate as a monomer unit.

* * * * *

UNITED STATES PATENT AND TRADEMARK OFFICE
CERTIFICATE OF CORRECTION

PATENT NO. : 8,580,281 B2  Page 1 of 1
APPLICATION NO. : 12/919723
DATED : November 12, 2013
INVENTOR(S) : Morimoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this
Twenty-second Day of September, 2015

Michelle K. Lee
*Director of the United States Patent and Trademark Office*